United States Patent [19]

Matsuura et al.

[11] Patent Number: 4,997,802

[45] Date of Patent: Mar. 5, 1991

[54] CATALYST FOR PREPARATION OF HYDROCARBONS

[75] Inventors: Ikuya Matsuura, Toyama; Yasushi Yoshida, Ube, both of Japan

[73] Assignee: UBE Industries, Ltd., Japan

[21] Appl. No.: 553,323

[22] Filed: Jul. 17, 1990

Related U.S. Application Data

[62] Division of Ser. No. 279,753, Dec. 5, 1988.

[30] Foreign Application Priority Data

Dec. 11, 1987 [JP] Japan .................................. 62-312127

[51] Int. Cl.$^5$ ........................ B01J 23/02; B01J 23/04
[52] U.S. Cl. .................................. 502/303; 502/302; 502/306; 502/324; 502/328; 502/340; 502/341; 502/343
[58] Field of Search ............... 502/302, 303, 304, 306, 502/324, 328, 340, 341, 343

[56] References Cited

U.S. PATENT DOCUMENTS

| | | | |
|---|---|---|---|
| 4,450,310 | 5/1984 | Fox et al. | 502/304 X |
| 4,774,216 | 9/1988 | Kolts et al. | 502/340 X |
| 4,780,449 | 10/1988 | Hicks | 502/341 X |

*Primary Examiner*—W. J. Shine
*Attorney, Agent, or Firm*—Finnegan, Henderson, Farabow, Garrett & Dunner

[57] ABSTRACT

A process for preparing hydrocarbons having at least two carbon atoms by bringing a methane-containing gas maintained at a temperature of 500° to 1500° C. into contact with an oxygen-containing gas in the presence of a catalyst to effect oxidative coupling, using a catalyst comprising (1) a single-crystal, high-purity, and ultra-fine powdery magnesium oxide obtained by the gas-phase method, and (2) an alkali metal oxide.

13 Claims, 1 Drawing Sheet

CATALYST FOR PREPARATION OF HYDROCARBONS

This is a division of application Ser. No. 07/279,753, filed Dec. 5, 1988, now issued.

BACKGROUND OF THE INVENTION

1. Field of the Invention

The present invention relates to a process for preparing hydrocarbons having at least 2 carbon atoms, such as ethylene, ethane and propylene, by bringing a methane-containing gas into contact with an oxygen-containing gas in the presence of a catalyst, and to a catalyst to be used when carrying out this process.

2. Description of the Related Art

Since an olefinic hydrocarbon, especially a lower olefinic hydrocarbon such as ethylene or propylene, has a carbon-to-carbon double bond and a rich reactivity, this olefinic hydrocarbon is an important basic material for petrochemical products. In the United States and Canada, wet natural gas (composed mainly of ethane and higher hydrocarbons) is abundantly available at a low cost, and the olefinic hydrocarbon is mainly prepared by processes using this wet natural gas as the starting material. In Japan and European countries, however, naphtha is used as the starting material and a process for thermally cracking naphtha is mainly adopted for the preparation of olefinic hydrocarbons.

Since the oil crisis of 1973, attempts have been made in many countries to use various materials other than naphtha or wet natural gas, and a process of promise is that for preparing ethylene from a dry natural gas (composed mainly of methane) as the starting material.

The exploitable amount of dry natural gas deposits is comparable to the present state of petroleum deposits, and new deposits are being discovered one after the other: It is estimated that the ultimate exploitable amount may be 200 trillion to 250 trillion cubic meters. This natural gas is broadly distributed all over the world, converse to the uneven distribution of petroleum, but nevertheless, this natural gas is still relatively little utilized.

Under this background, many countries are involved in research into the preparation of ethylene from dry natural gas, and various techniques therefore have been proposed in reports and patent specifications.

For example, G. E. Keller et al [J. of Catalysis, 73, 9 (1982)] reported that an alumina catalyst having an oxide of manganese (Mn) or cadmium (Cd) supported thereon is thought to be effective for the conversion (oxidative coupling), but the conversion of methane is low (lower than 5%) and the selectively for ethylene and ethane is very low (lower than 45%). Further, the temperature required for the reaction is relatively high (800° C). Moreover, after research into the activity of a lithium (Li)/magnesia (MgO) catalyst, prepared by a customary catalyst-preparing process, for the oxidative coupling of methane, Ito et al [J. Am. Chem. Soc., 107, 5062, (1985)] reported that use of a 7 weight-Li/MgO catalyst is most preferable and, at 720° C., the conversion of methane is 38% and the selectivity for ethylene and ethane (hereinafter referred to as "C2-selectivity") is 47%. As a result of similar experiments using magnesia catalysts having various oxides supported thereon, Aika et al [Chem. Lett., 1165 (1986)] reported that use of a 15 mole %-Na/MgO catalyst is preferable and that, at 800° C., a C2-selectivity of 57% and a C2-yield of 22.4% are obtained. Furthermore, Japanese Unexamined Patent Publication No. 61-207346 teaches that a catalyst having lead oxide (PbO) or lead oxide and manganese oxide (MnO) supported thereon is preferable, and a methane conversion of 26%, a C2-selectivity of 41%, and a C2-yield of 10.7% are obtained at 750° C. If the catalytic activities disclosed in the foregoing literature references and patent specifications are expressed in terms of the spacetime yield of ethylene and ethane (hereinafter referred to as "C2-STY"), it is seen that, where W/F>0.5 g.h/l (W stands for the weight of the catalyst and F stands for the flow rate of the circulated gas), the C2-STY is lower than 3 millimole/g.h, although the reaction temperature is relatively high, and thus the catalytic performance is not satisfactory.

As a recently reported catalyst giving a relatively high C2-STY, there can be mentioned a lanthanum aluminate ($LaAlO_3$) type catalyst proposed by Imai et al [J. Chem. Soc. Commun. (1986)], which gives a C2-STY of 8.31 millimole/g.h (710° C., W/F=0.125 g.h/l); a 20 weight %-PbO/MgO catalyst disclosed in Japanese Unexamined Patent Publication No. 61-165341, which gives a C2-STY of 10.3 millimole/g.h (717° C., W/F=0.072 g.h/l); a 20 weight %-PbO/MgO catalyst proposed by Asami et al [Chem. Lett., 1233 (1986)], which gives a C2-STY of 11.1 millimole/g.h (760° C., W/F=0.0446 g.h/l); and, a bismuth oxide/potassium carbonate/alumina catalyst (7 weight %-$Bi_2O_3$ weight %-$K_2CO_3$/$\gamma$-$Al_2O_3$) proposed by I. T. A. Emesh et al [J. Phys. Chem., 90, 4785 (1986)], which gives a C2-STY of 90.0 millimole/g.h (700° C., W/F=0.00292 g.h/l). In each of these catalysts, however, the conversion of methane is low (lower than 25%) and the C2-yield is low (lower than 13%), and therefore, the C2-STY is lower than 100 millimole/g.h.

The highest C2-STY heretofore reported is 86 to 2980 millimole/g.h (750° C., W/F =0.000223 to 0.0891 g.h/l) given by a samarium oxide ($Sm_2O_3$) catalyst proposed by Otsuka et al [Chem. Lett., 483 (1987)]. In this catalyst, however, the conversion of methane is low (lower than 18%) and the C2-yield is low (lower than 11%), and especially at the maximum C2-STY value, the conversion of methane is about 5.5% and the C2-yield is about 3.4%, which are both very low. Furthermore, the $Sm_2O_3$ of this catalyst is a rare earth element oxide, which is very difficult to find and therefore exists in only very small amounts and thus is very expensive. Accordingly, the preparation of ethylene on an industrial scale by using this $Sm_2O_3$ catalyst is very difficult.

SUMMARY OF THE INVENTION

The basic principle of the process for the preparation of hydrocarbons according to the present invention resides in tho known process called "the oxidative coupling of methane", in which hydrocarbons having at least 2 carbon atoms are prepared by bringing a methane-containing gas maintained at 500° to 1500° C. into contact with an oxygen-containing gas in the presence of a catalyst. As pointed out hereinbefore, however, the known techniques involve the several problems described below; i.e., (1) the conversion of methane is low, (2) the C2-selectivity is low, (3) the C2-STY is low, (4) the temperature for the reaction is high, (5) the life of the catalyst is short, and (6) a catalyst giving a relatively high methane conversion, C2-selectivity, and C2-STY is very expensive and cannot be practically used. The present invention solves all of these problems, since, in accordance with the present invention, there is provided a process for the preparation of hydrocarbons having at least 2 carbon atoms, such as ethylene and ethane, which comprises bringing a methane-containing gas maintained at a temperature of 500° to 800° C. into contact with an oxygen-containing gas in the presence of a catalyst prepared by using a gas-phase oxidation method to obtain a single-crystal, high-purity, and ultra-fine powdery magnesium oxide to effect oxidative coupling.

Furthermore, in accordance with the present invention, there is provided a catalyst which can be advantageously used for carrying out the above-mentioned process.

BRIEF DESCRIPTION OF THE DRAWING

The drawing illustrates an example of the structure of the double-tube burner used for the production of the single-crystal, high-purity, and ultra-fine powdery magnesium oxide which is a component of the catalyst of the present invention.

DESCRIPTION OF THE PREFERRED EMBODIMENTS

Figure 1:
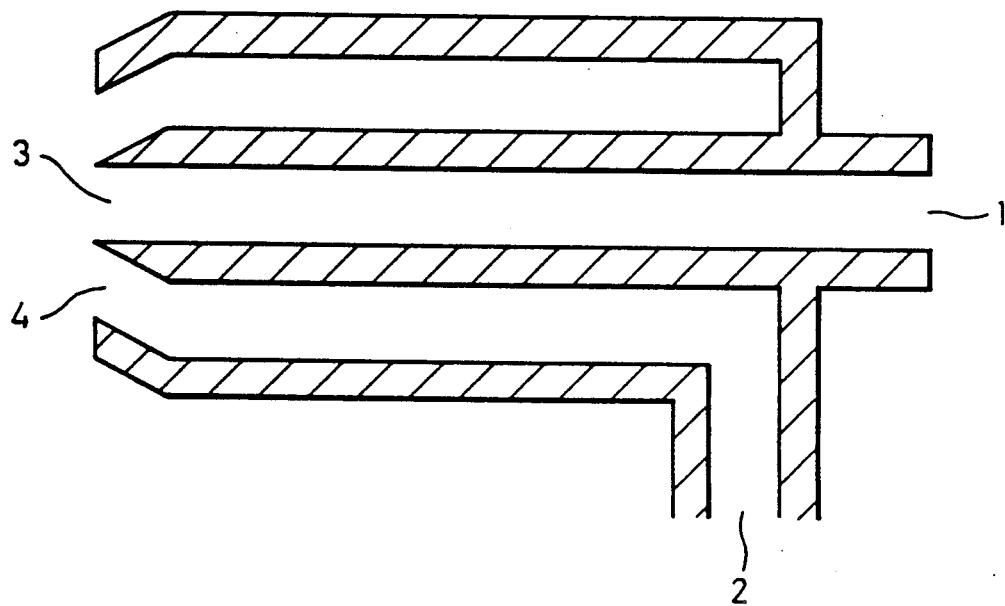

The catalyst of the present invention will now be described.

This catalyst is prepared by using a gas-phase oxidation method to obtain a single-crystal, high-purity, and ultra-fine powdery magnesium oxide as the indispensable component starting material, adding additive component starting materials capable of forming an alkali metal oxide as the second component and, if desired, an oxide of an metal element having an atomic number of 21 (Sc) to 30 (Zn) or 57 (La) to 71 (Lu) and a positive divalency or positive trivalency, after the preparation of the catalyst.

The magnesium oxide as the indispensable component starting material of the present invention is obtained by bringing a vapor of magnesium into contact with an oxygen-containing gas in a turbulently diffused state to oxidize magnesium. For example, a method can be adopted in which a vapor of magnesium and an oxygen-containing gas are jetted from independent jet openings, and are brought into contact with each other in a turbulently diffused state to form a turbulently diffused flame, and the vapor of magnesium is oxidized in this flame. The magnesium oxide prepared by this gas-phase oxidation method is characterized by a single crystal form, a high purity, an ultra-fine powdery state, and a high activity (the average particle size is 0.01 to 0.2 μm and the purity is higher than 99.98%). Note, an ultra-fine powder having a finer size is most preferable as the magnesium oxide starting material.

The preparation of magnesium oxide by the above-mentioned gas-phase oxidation of magnesium vapor can be carried out, for example, by using a double-tube burner shown in the accompanying drawing. More specifically, a vapor of magnesium generated within a retort (not shown in the drawing) is introduced from a metal vapor-introducing opening 1, and an oxygen-containing gas is introduced from an oxygen-containing gas-introducing opening 2. The introduced magnesium vapor and oxygen-containing gas are independently jetted from a metal vapor-jetting nozzle 3 and an oxygen-containing gas-jetting nozzle 4, respectively, and thus are brought into contact with each other in a turburently diffused state. The magnesium vapor and oxygen-containing gas supplied in this state form a turbulently diffused flame in this contact area, and accordingly, the magnesium vapor is oxidized to become magnesium oxide.

As the starting material capable of forming an alkali metal oxide after the preparation of the catalyst, which is used as one additive component starting material for the preparation of the catalyst used in the present invention, there can be used oxides, hydroxides, carbonates, nitrates, acetates, alkoxides, and acetylacetonates of lithium (Li), sodium (Na), potassium (K), and rubidium (Rb). By adding an alkali metal oxide to the catalyst, using the above-mentioned starting material, the C2-yield and C2-STY are dramatically increased.

As the starting material capable of forming an oxide of a metal element having an atomic number of 21 (Sc) to 30 (Zn) or 57 (La) to 71 (Lu) and a positive divalency or positive trivalency, there can be mentioned oxides, hydroxides, nitrates, acetates, alkoxides, and acetylacetonates of these metal elements, such as iron (Fe), cobalt (Co), nickel (Ni), copper (Cu), zinc (Zn), lanthanum (La), cerium (Ce), and samarium (Sm). The incorporation of a metal oxide as mentioned above into the catalyst, makes it possible to advance the oxidative coupling reaction of methane even at a lower temperature.

Preferably, each of the additive component starting materials for the preparation of the catalyst is added in an amount such that the content of the metal element is 1 to 20 mole %, especially 1 to 10 mole %, after the preparation of the catalyst. The amounts of the supported metal elements can be reduced in the catalyst of the present invention and are smaller than about one half of the supported amounts necessary in the conventional techniques. The preparation of the catalyst can be accomplished by customary methods such as kneading and impregnation.

In the process for preparing ethylene and other hydrocarbons according to the present invention, a methane-containing gas such as dry natural gas is brought into contact with an oxygen-containing gas such as air in the presence of the above-mentioned catalyst. The reaction is usually carried out in a continuous manner by introducing the above-mentioned mixed gas, if necessary together with a diluent gas, into a packed tube type circulation reactor (fixed bed type). The reaction pressure is usually from atmospheric pressure to 20 kgf/cm$^2$G, preferably from atmospheric pressure to 5 kgf/cm$^2$G, and the reaction temperature is usually 500° to 900° C., preferably 500° to 800° C.

A fluidized bed type reactor also can be used as the reaction apparatus, i.e., the reaction apparatus is not limited to the above-mentioned fixed bed type reactor. By carrying out an oxidative coupling of the methane-containing gas by the above-mentioned process, hydrocarbons such as ethylene can be prepared at a relatively low temperature with the use of a small amount of the catalyst at a high conversion and a high selectivity, and thus a high STY value.

The gas-phase oxidation method used to obtain a high-purity, ultra-fine powdery magnesium oxide single crystal provides a semi-crystal site for promoting the growth of the crystal, and $Mg^{2+}$ and $O^{2-}$ ions located at this site are in the tri-coordinated state and are also in the activated state as the coordination-unsaturated ions (expressed as $Mg_{3c}^{2+}$ and $O_{3c}^{2-}$). It is considered that this $Mg_{3c}^{2+}$ having a high activity acts as an active site for the adsorption of methane.

When an alkali metal is added to MgO, the alkali metal ion is strongly adsorbed in coordination-unsaturated $O_{3c}^{2-}$ to form an alkali metal oxide layer on the semi-crystal face of the single crystal of MgO. This oxide of the alkali metal (A) is kept in the state ($A^+O^--A^{\cdot}$) at a high temperature to form an oxygen ion ($O^-$) having a negative monovalency, and this $O^-$ pulls out hydrogen from methane adsorbed in coordination-unsaturated $Mg_{3c}^{2+}$ to convert the methane to a methyl radical ($CH_3\cdot$). Subsequent dimerization of the so-formed $CH_3\cdot$ causes the formation of hydrocarbons having at least 2 carbon numbers, such as ethane and ethylene.

An ion of a metal having an atomic number of 26 (Fe) to 30 (Zn) and a positive divalency, can easily replace the $Mg^{2+}$ ion in magnesium oxide by calcination at the catalyst-preparing step, and further, activates the neighboring coordination-unsubstituted $Mg_{3c}^{2+}$ to facilitate the adsorption of methane, and thus it is considered that the oxidative coupling reaction of methane can be advanced even at a lower temperature. A metal ion ($M^{3+}$) having an atomic number of 21 (Sc) to 28 (Ni) or 57 (La) to 71 (Lu), and a positive trivalency, and an alkali metal ion ($A^+$) form $A^+M^{3+}O_2$ at the initial stage of calcination at the catalyst-preparing step, and since this composite oxide has an NaCl type crystal structure as well as magnesium oxide, both easily form a solid solution. This solid solution further activates the above-mentioned unsaturated ion and $O^-$ ion, and therefore, it is considered that the oxidative coupling reaction of methane is further promoted.

The following effects can be attained by preparing hydrocarbons having at least two carbon atoms according to the process of the present invention.

(1) The conversion of methane is high.
(2) The C2-selectivity is high.
(3) The C2-STY value is large.
(4) The temperature required for the reaction is very low.
(5) The catalyst has a long life.
(6) The amount of the metal element supported in the catalyst is very small.
(7) The catalyst is available at a relatively low price and thus the problem of cost is practically eliminated.

The present invention will now be described in detail with reference to the following examples, that by no means limit the scope of the invention.

EXAMPLE 1

A double-tube burner having a structure shown in the drawing was used for this example, wherein the diameter of an inner nozzle for jetting a metal vapor (magnesium vapor) was 4 mm, and the diameter of an outer nozzle for jetting an oxygen-containing gas (air) was 20 mm.

Metallic magnesium was placed in a retort and heated at 1200° C. to generate a magnesium vapor at a rate of 1.2 g/min, and the vapor was introduced into a metal vapor-introducing tube of the above-mentioned burner and jetted at a rate of 7.6 m/sec from the metal vapor-jetting nozzle.

Air as the oxygen-containing gas was jetted from the oxygen-containing gas-jetting nozzle at a rate of 12 m/sec so that the ratio of the partial pressure of oxygen to the partial pressure of the magnesium vapor, i.e., $[O_2]/[Mg]$, was 7 in the oxygen-containing gas, whereby the magnesium vapor was brought into contact with air in the turbulently diffused state to form a flame and prepare a fine particulate magnesium oxide. The resultant magnesium oxide was collected by a collecting apparatus.

A turbulently diffused flame was formed and had a length of 4.0 cm. The average particle size of the obtained fine particulate magnesium oxide (MgO) was 0.035 μm.

Note, the average particle size was calculated by the following formula, from the specific surface area determined by the nitrogen adsorption method:

Average particle size = $a/(S \times \rho)$ wherein S stands for the specific surface area, a represents the shape coefficient, which is 6, and $\rho$ stands for the particle density, which is 3.58 g/cm$^3$.

EXAMPLES 2 THROUGH 6

To 4.03 g of a single-crystal, high-purity, and ultra-fine powdery magnesium oxide (having an average particle size of 0.01 μm) prepared in the same manner as described in Example 1 was added an ethanol solution of lithium acetylacetonate, and the elements were homogeneously and thoroughly mixed, granulated, and dried at 100° C. The dried product was calcined in air at 800° C. for 2 hours to obtain 4.10 g of an MgO catalyst containing lithium (Li) at a content of 5 mole %. Then, 0.01 g of this 5 mole %-Li/MgO catalyst was charged in a fixed bed type circulation reactor, and a mixed gas having a $CH_4/O_2$ ratio of 2 was circulated at a rate of 50 ml/min under a pressure of 1 atmosphere. When the products obtained at reaction temperatures of 600°, 650°, 700°, 750°, and 800° C. were analyzed by gas chromatography, it was found that the products comprised ethylene ($C_2H_4$), ethane ($C_2H_6$), carbon dioxide ($CO_2$), carbon monoxide (CO), and water ($H_2O$).

The results are shown in Table 1.

TABLE 1

| Example No. | Reaction Temperature (°C.) | Conversion (%) $CH_4$ | Conversion (%) $O_2$ | $C_2$-Yield (%) | $C_2$-Selectivity (%) $C_2H_6$ | $C_2$-Selectivity (%) $C_2H_4$ | $C_2$-STY (mmol/g · h) |
|---|---|---|---|---|---|---|---|
| 2 | 600 | 3.1 | 10.7 | 0.5 | 15.0 | 1.0 | 22 |
| 3 | 650 | 16.0 | 35.2 | 8.0 | 30.1 | 20.0 | 359 |
| 4 | 700 | 33.9 | 76.2 | 19.0 | 15.7 | 40.2 | 848 |
| 5 | 750 | 39.6 | 94.6 | 20.6 | 11.5 | 40.5 | 920 |
| 6 | 800 | 39.5 | 95.0 | 20.5 | 9.0 | 43.5 | 916 |

EXAMPLES 7 THROUGH 9 AND COMPARATIVE EXAMPLE 1

Li/MgO catalysts were prepared in the same manner as described in Example 4 except that the amount supported of Li was changed from 5 mole % to 0, 1, 10, or 20 mole %, and the catalytic activities were similarly tested. The results are shown in Table 2.

TABLE 2

| No. | Amount (mole %) of Supported Li (mol %) | Conversion (%) CH$_4$ | Conversion (%) O$_2$ | C$_2$-Yield (%) | C$_2$-Selectivitiy (%) C$_2$H$_6$ | C$_2$-Selectivitiy (%) C$_2$H$_4$ | C$_2$-STY (mmol/g · h) |
|---|---|---|---|---|---|---|---|
| Comparative Example 1 | 0 | 10.9 | 32.5 | 3.5 | 14.5 | 19.5 | 156 |
| Example 7 | 1 | 24.9 | 59.2 | 12.6 | 14.3 | 36.8 | 563 |
| Example 8 | 10 | 35.1 | 77.6 | 19.6 | 15.6 | 40.3 | 880 |
| Example 9 | 20 | 33.1 | 73.3 | 18.8 | 15.8 | 41.1 | 844 |

Note
reaction temperature: 700° C.

EXAMPLES 10 THROUGH 13

Catalysts were prepared in the same manner as described in Example 2 except that, instead of the single-crystal, high-purity, and ultra-fine powdery magnesium oxide having an average particle size of 0.01 μm prepared in the same manner as described in Example 1, a similarly prepared magnesium oxide having an average particle size of 0.05 or 0.10 μm was used, and the catalytic activities were tested at reaction temperatures of 700° and 750° C. under the same conditions as adopted in Examples 4 and 5.

The results are shown in Tables 3 and 4.

TABLE 3

| Example No. | Average Particle Size (μm) of Gas-Phase Oxidation Method Magnesium Oxide | Conversion (%) CH$_4$ | Conversion (%) O$_2$ | C$_2$-Yield (%) | C$_2$-Selectivity (%) C$_2$H$_6$ | C$_2$-Selectivity (%) C$_2$H$_4$ | C$_2$-STY (mmol/g · h) |
|---|---|---|---|---|---|---|---|
| 10 | 0.05 | 34.0 | 82.0 | 18.6 | 15.9 | 38.8 | 831 |
| 11 | 0.10 | 29.0 | 70.6 | 14.5 | 14.0 | 36.0 | 648 |

Note
reaction temperature: 700° C.

TABLE 4

| Example No. | Average Particle Size (μm) of Gas-Phase Oxidation Method Magnesium Oxide | Conversion (%) CH$_4$ | Conversion (%) O$_2$ | C$_2$-Yield (%) | C$_2$-Selectivity (%) C$_2$H$_6$ | C$_2$-Selectivity (%) C$_2$H$_4$ | C$_2$-STY (mmol/g · h) |
|---|---|---|---|---|---|---|---|
| 12 | 0.05 | 38.7 | 92.3 | 20.1 | 11.4 | 40.6 | 898 |
| 13 | 0.10 | 37.5 | 88.8 | 19.8 | 11.6 | 41.2 | 885 |

Note
reaction temperature: 750° C.

COMPARATIVE EXAMPLES 2 AND 3

Aqueous ammonia was added to an aqueous solution of magnesium nitrate to form magnesium hydroxide, and the magnesium hydroxide was calcined at 800° C. to obtain a liquid-phase method magnesium oxide (having an average particle size of 0.02 μm). An Li/MgO catalyst was prepared by using this liquid-phase method magnesium oxide, in the same manner as described in Example 2.

Separately, an ethanol solution of lithium acetylacetonate was added to a commercially available silica gel, and these elements were homogeneously and thoroughly mixed, granulated, and dried at 100° C. The dried product was calcined in air for 2 hours to obtain an SiO$_2$ catalyst containing 5 mole % of lithium (Li).

The catalytic activities were tested by using these two catalysts in the same manner as described in Example 4.

The results are shown in Table 5.

TABLE 5

| Comparative Example No. | Catalyst | Conversion (%) CH$_4$ | Conversion (%) O$_2$ | C$_2$-Yield (%) | C$_2$-Selectivity (%) C$_2$H$_6$ | C$_2$-Selectivity (%) C$_2$H$_4$ | C$_2$-STY (mmol/g · h) |
|---|---|---|---|---|---|---|---|
| 2 | 5 mole %-Li/liquid-phase oxidation method MgO | 9.2 | 20.1 | 4.4 | 16.4 | 31.6 | 196 |
| 3 | 5 mole %-Li/SiO$_2$ | 1.7 | 4.8 | 0.5 | 11.2 | 16.8 | 22 |

Note
reaction temperature: 700° C.

EXAMPLES 14 THROUGH 16

The procedures of Example 4 were repeated in the same manner except that sodium acetylacetonate, potassium acetylacetonate or rubidium acetyl acetonate was used instead of lithium acetylacetonate, and the catalytic activities of the obtained 5 mole %-alkali metal/MgO catalysts were tested in the same manner as in Example 4.

The results are shown in Table 6.

TABLE 6

| Example No. | Catalyst | Conversion (%) CH$_4$ | Conversion (%) O$_2$ | C$_2$-Yield (%) | C$_2$-Selectivity (%) C$_2$H$_6$ | C$_2$-Selectivity (%) C$_2$H$_4$ | C$_2$-STY (mmol/g · h) |
|---|---|---|---|---|---|---|---|
| 14 | 5 mole %-Na/MgO | 31.0 | 80.8 | 14.8 | 21.5 | 26.2 | 662 |
| 15 | 5 mole %-K/MgO | 31.4 | 81.7 | 13.7 | 18.9 | 24.9 | 612 |

TABLE 6-continued

| Example No. | Catalyst | Conversion (%) CH$_4$ | Conversion (%) O$_2$ | C$_2$-Yield (%) | C$_2$-Selectivity (%) C$_2$H$_6$ | C$_2$-Selectivity (%) C$_2$H$_4$ | C$_2$-STY (mmol/g · h) |
|---|---|---|---|---|---|---|---|
| 16 | 5 mole %-Rb/MgO | 30.7 | 81.0 | 13.4 | 18.8 | 24.9 | 600 |

Note
reaction temperature: 700° C.

EXAMPLES 17 THROUGH 19

A 5 mole %-Li/MgO catalyst was prepared in the same manner as described in Example 4 except that an ethanol solution of lithium acetate, an aqueous solution of lithium nitrate or an aqueous solution of lithium carbonate was used instead of the ethanol solution of lithium acetylacetonate, and the catalytic activities were tested in the same manner as described in Example 4.

The results are shown in Table 7.

TABLE 7

| Example No. | Lithium Salt for preparation of Catalyst | Conversion (%) CH$_4$ | Conversion (%) O$_2$ | C$_2$-Yield (%) | C$_2$-Selectivity (%) C$_2$H$_6$ | C$_2$-Selectivity (%) C$_2$H$_4$ | C$_2$-STY (mmol/g · h) |
|---|---|---|---|---|---|---|---|
| 17 | Lithium acetate | 33.2 | 74.1 | 18.5 | 15.6 | 40.3 | 827 |
| 18 | Lithium nitrate | 33.5 | 77.1 | 17.9 | 14.8 | 40.2 | 800 |
| 19 | Lithium carbonate | 32.4 | 77.8 | 16.5 | 14.0 | 37.0 | 738 |

Note
reaction temperature: 700° C.

EXAMPLES 20 THROUGH 22

By using a 5 mole %-Li/MgO catalyst prepared in the same manner as described in Example 4, the catalytic activity test was conducted at 700° C. and the dependency of the activity on the reaction time was examined.

The results are shown in Table 8.

TABLE 8

| Example No. | Reaction Time (hours) | Conversion (%) CH$_4$ | Conversion (%) O$_2$ | C$_2$-Yield (%) | C$_2$-Selectivity (%) C$_2$H$_6$ | C$_2$-Selectivity (%) C$_2$H$_4$ | C$_2$-STY (mmol/g · h) |
|---|---|---|---|---|---|---|---|
| 20 | 1 | 35.1 | 77.6 | 19.0 | 14.3 | 36.7 | 853 |
| 21 | 150 | 33.6 | 76.7 | 18.4 | 15.9 | 38.8 | 822 |
| 22 | 500 | 33.8 | 77.2 | 18.5 | 15.4 | 37.0 | 727 |

Note
reaction temperature: 700° C.

EXAMPLES 23 THROUGH 36

An ethanol solution of lithium acetylacetonate was added to a single-crystal, high-purity, and ultra-fine powdery magnesium oxide (having an average particle size of 0.01 μm) prepared in the same manner as described in Example 1, and zinc acetate, nickel acetylacetonate or copper acetylacetonate was further added and homogeneously and thoroughly mixed, granulated, and dried at 100° C. The dried product was calcined at 800° C. in air to obtain MgO catalyst containing 5 mole % of lithium and 5 mole % of the metal (M) indicated above. By using 0.01 g of this 5 mole %-Li/5 mole %-M/MgO catalyst, the catalytic activity test was carried out at 500° to 700° C. in the same manner as described in Example 2.

The results are shown in Table 9.

TABLE 9

| Example No. | Catalyst | Reaction Temperature (°C.) | Conversion (%) CH$_4$ | Conversion (%) O$_2$ | C$_2$-Yield (%) | C$_2$-Selectivity (%) C$_2$H$_6$ | C$_2$-Selectivity (%) C$_2$H$_4$ | C$_2$-STY (mmol/g · h) |
|---|---|---|---|---|---|---|---|---|
| 23 | 5 mole %-Li/5 mole %-Zn/MgO | 500 | 11.1 | 36.8 | 2.0 | 15.0 | 3.0 | 89 |
| 24 | | 550 | 17.8 | 51.4 | 5.0 | 19.0 | 9.0 | 224 |
| 25 | | 600 | 22.5 | 61.0 | 9.1 | 20.3 | 24.1 | 407 |
| 26 | | 650 | 35.4 | 86.9 | 17.0 | 20.6 | 27.6 | 760 |
| 27 | | 700 | 35.3 | 83.6 | 18.0 | 21.4 | 29.3 | 805 |
| 28 | 5 mole %-Li/5 mole %-Ni/MgO | 500 | 11.0 | 37.0 | 2.0 | 15.0 | 3.0 | 89 |
| 29 | | 550 | 20.8 | 63.8 | 5.0 | 19.1 | 7.1 | 224 |
| 30 | | 600 | 25.0 | 74.4 | 8.5 | 20.2 | 13.8 | 380 |
| 31 | | 650 | 31.0 | 82.1 | 13.0 | 22.8 | 19.3 | 581 |
| 32 | | 700 | 33.6 | 84.7 | 15.5 | 20.2 | 25.8 | 698 |
| 33 | 5 mole %-Li/5 mole-Cu/MgO | 550 | 12.5 | 42.0 | 2.0 | 17.0 | 3.0 | 89 |
| 34 | | 600 | 25.0 | 78.4 | 6.5 | 15.2 | 10.8 | 291 |
| 35 | | 650 | 30.3 | 88.8 | 10.0 | 17.5 | 15.5 | 447 |
| 36 | | 700 | 33.8 | 91.5 | 13.0 | 18.5 | 21.7 | 603 |

EXAMPLES 37 THROUGH 46

The procedures of Examples 23 through 36 were repeated in the same manner except that samarium acetate or cerium acetylacetonate was used instead of zinc acetate or the like, and the catalytic activities of the obtained 5 mole %-Li/5 mole %-M/MgO catalyst were tested in the same manner as described in Examples 23 through 36.

The results are shown in Table 10.

TABLE 10

| Example No. | Catalyst | Reaction Temperature (°C.) | Conversion (%) CH₄ | O₂ | C₂-Yield (%) | C₂-Selectivity (%) C₂H₆ | C₂H₄ | C₂-STY (mmol/g · h) |
| --- | --- | --- | --- | --- | --- | --- | --- | --- |
| 37 | 5 mole %-Li/5 mole %-Sm/MgO | 500 | 5.0 | 18.2 | 0.5 | 9.0 | 1.0 | 22 |
| 38 | | 550 | 18.8 | 31.6 | 3.1 | 17.0 | 3.1 | 139 |
| 39 | | 600 | 23.3 | 67.1 | 7.5 | 26.4 | 6.6 | 335 |
| 40 | | 650 | 30.9 | 79.9 | 13.3 | 25.6 | 17.2 | 595 |
| 41 | | 700 | 39.7 | 98.2 | 18.3 | 23.0 | 23.0 | 810 |
| 42 | 5 mole %-Li/5 mole %-Ce/MgO | 500 | 4.2 | 15.0 | 0.5 | 10.0 | 2.0 | 22 |
| 43 | | 550 | 18.2 | 57.9 | 4.0 | 18.2 | 4.1 | 179 |
| 44 | | 600 | 22.5 | 59.6 | 9.0 | 32.0 | 8.0 | 402 |
| 45 | | 650 | 32.9 | 80.6 | 15.5 | 28.2 | 18.8 | 693 |
| 46 | | 700 | 41.9 | 97.8 | 20.1 | 23.8 | 23.6 | 898 |

COMPARATIVE EXAMPLES 4 AND 5

Samarium acetylacetonate was calcined at 800° C. for 2 hours in an electric furnace to obtain a samarium oxide catalyst.

Separately, an ethanol solution of samarium acetate was added to gas-phase oxidation method magnesium oxide (having an average particle size of 0.01 μm), and a 5 mole %-Sm/MgO catalyst was prepared from the mixture in the same manner as described in Example 2.

The catalytic activity test was carried out by using these two catalysts in the same manner as described in Example 4.

The results are shown in Table 11.

TABLE 11

| Comparative Example No. | Catalyst | Conversion (%) CH₄ | O₂ | C₂-Yield (%) | C₂-Selectivity (%) C₂H₆ | C₂H₄ | C₂-STY (mmol/g · h) |
| --- | --- | --- | --- | --- | --- | --- | --- |
| 4 | Sm₂O₃ | 25.0 | 66.8 | 10.5 | 15.1 | 26.9 | 469 |
| 5 | 5 mole %-Sm/MgO | 25.5 | 65.8 | 11.5 | 15.8 | 29.3 | 514 |

Note
reaction temperature: 700° C.

EXAMPLES 47 THROUGH 49

The procedures of Example 4 were repeated in the same manner except that an ethanol solution of sodium alkoxide, an methanol solution of potassium acetate or an ethanol solution of rubidium hydroxide was used instead of the ethanol solution of lithium acetylacetonate, and the catalytic activity test was carried out by using the obtained 5 mole %-alkali metal/MgO catalysts in the same manner as in Example 4.

The results are shown in Table 12.

TABLE 12

| Example No. | Catalyst | Conversion (%) CH₄ | O₂ | C₂-Yield (%) | C₂-Selectivity (%) C₂H₆ | C₂H₄ | C₂-STY (mmol/g · h) |
| --- | --- | --- | --- | --- | --- | --- | --- |
| 47 | 5 mole %-Na/MgO | 29.8 | 80.5 | 14.4 | 22.1 | 26.3 | 643 |
| 48 | 5 mole %-K/MgO | 31.1 | 81.9 | 13.2 | 17.3 | 25.0 | 589 |
| 49 | 5 mole %-Rb/MgO | 30.0 | 79.5 | 12.6 | 18.1 | 23.8 | 563 |

Note
reaction temperature: 700° C.

We claim:

1. A catalyst for preparing hydrocarbons having at least two carbon atoms by bringing a methane-containing gas maintained at a temperature of 500° to 1500° C. into contact with an oxygen-containing gas to effect oxidative coupling, which comprises (1) a single-crystal, high-purity, and ultra-fine powdery magnesium oxide obtained by the gas-phase oxidation method, and (2) an alkali metal oxide.

2. A catalyst as set forth in claim 1, wherein the alkali metal oxide is contained in an amount of 1 to 20 mole % as the alkali metal element.

3. A catalyst as set forth in claim 2, wherein the content of the alkali metal element is 1 to 10 mole %.

4. A catalyst as set forth in claim 1, wherein the magnesium oxide is obtained by bringing a vapor of magnesium into contact with an oxygen-containing gas in a turbulently diffused state, to oxidize the magnesium vapor.

5. A catalyst as set forth in claim 4, wherein the magnesium oxide has an average particle size of 0.01 to 0.2 μm and a purity of at least 99.98.

6. A catalyst as set forth in claim 1, wherein the alkali metal oxide is prepared from one of an oxide, hydroxide, carbonate, nitrate, acetate, alkoxide and acetylacetonate of lithium (Li), sodium (Na), potassium (K) and rubidium (Rb).

7. A catalyst for preparing hydrocarbons having at least two carbon atoms by bringing a methane-containing gas maintained at a temperature of 500° to 1500° C. into contact with an oxygen-containing gas to effect oxidative coupling, which comprises (1) a single-crystal, high-purity, and ultra-fine powdery magnesium oxide obtained by the gas-phase oxidation method, (2) an alkali metal oxide, and (3) at least one oxide selected from the group consisting of oxide of metal elements having atomic number of 21 (Sc) to 30 (Zn) and metal elements having an atomic number of 57 (La) to 71 (Lu), and having a positive divalency or positive trivalency.

8. A catalyst as set forth in claim 7, wherein the alkali metal oxide (2) is contained in an amount of 1 to 20 mole % as the alkali metal element and the metal element oxide (3) is contained in an amount of 1 to 20 mole % as the metal element.

9. A catalyst as set forth in claim 8, wherein the content of the alkali metal content is 1 to 10 mole % and the content of the metal element is 1 to 10 mole %.

10. A catalyst as set forth in claim 7, wherein the magnesium oxide is obtained by bringing a vapor of magnesium into contact with an oxygen containing gas in a turbulently diffused state, to oxidize the magnesium vapor.

11. A catalyst as set forth in claim 10, wherein the magnesium oxide has an average particle size of 0.01 to 0.2 $\mu$m and a purity of at least 99.98%.

12. A catalyst as set forth in claim 7, wherein the alkali metal oxide (2) is prepared from one of an oxide, hydroxide, carbonate, nitrate, acetate, alkoxide and acetylacetonate of lithium (Li), sodium (Na), potassium (K) and rubidium (Rb).

13. A catalyst as set forth in claim 7, wherein the metal element oxide (3) is prepared from one of an oxide, hydroxide, nitrate, acetate, alkoxide and acetylacetonate of iron (Fe), cobalt (Co), nickel (Ni), copper (Cu), zinc (Zn), lanthanum (La), cerium (Ce) and samarium (Sm).

* * * * *